(12) United States Patent
Takayama et al.

(10) Patent No.: US 7,945,147 B2
(45) Date of Patent: May 17, 2011

(54) IMAGE PICK UP UNIT

(75) Inventors: Masaki Takayama, Hachioji (JP); Satoshi Takekoshi, Hachioji (JP)

(73) Assignee: Olympus Medical Systems Corp. (JP)

( * ) Notice: Subject to any disclaimer, the term of this patent is extended or adjusted under 35 U.S.C. 154(b) by 964 days.

(21) Appl. No.: 11/782,968

(22) Filed: Jul. 25, 2007

(65) Prior Publication Data

US 2008/0025159 A1    Jan. 31, 2008

(30) Foreign Application Priority Data

Jul. 31, 2006    (JP) ................................. 2006-208852

(51) Int. Cl.
*A61B 1/04*    (2006.01)
*A62B 1/04*    (2006.01)

(52) U.S. Cl. ............................................ 396/17; 348/65
(58) Field of Classification Search ................... 396/17; 348/65
See application file for complete search history.

(56) References Cited

U.S. PATENT DOCUMENTS

| | | | | |
|---|---|---|---|---|
| 4,634,221 A | | 1/1987 | Hopfner | 350/255 |
| 4,828,360 A | * | 5/1989 | Maruyama | 359/824 |
| 4,841,323 A | * | 6/1989 | Yamada et al. | 396/90 |
| 5,706,143 A | * | 1/1998 | Hipp | 359/824 |
| 7,146,097 B2 | * | 12/2006 | Kameyama | 396/133 |
| 7,154,199 B2 | * | 12/2006 | Yasuda | 310/12.24 |
| 2006/0115259 A1 | * | 6/2006 | Ito et al. | 396/75 |
| 2006/0138873 A1 | * | 6/2006 | Yasuda | 310/12 |

FOREIGN PATENT DOCUMENTS

| | | |
|---|---|---|
| DE | 19718189 | 12/1997 |
| JP | 60243612 | 12/1985 |
| JP | 2003-131111 | 5/2003 |
| JP | 2004-97292 | 4/2004 |
| WO | 2005/060242 | 6/2005 |

OTHER PUBLICATIONS

Search Report dated Nov. 28, 2007 issued in counterpart European Application No. 07013216.2-2217.

\* cited by examiner

*Primary Examiner* — Rodney E Fuller
(74) *Attorney, Agent, or Firm* — Ostrolenk Faber LLP

(57) ABSTRACT

An image pick up unit includes an optical member, a holding member holding the optical member and movable in an axial direction of an optical axis of the optical member, a driving member rotatable about the optical axis, a cam mechanism configured to convert rotation of the driving member about the optical axis to movement of the holding member in the axial direction of the optical axis, a coil provided in the driving member and movable together with the driving member, and a magnetic field generation portion provided along a rotating direction of the coil and configured to generate a magnetic field to interact with a current flowing in the coil to drive the coil in the rotating direction.

7 Claims, 5 Drawing Sheets

IMAGE PICK UP UNIT

CROSS-REFERENCE TO RELATED APPLICATIONS

This application is based upon and claims the benefit of priority from prior Japanese Patent Application No. 2006-208852, filed Jul. 31, 2006, the entire contents of which are incorporated herein by reference.

BACKGROUND OF THE INVENTION

1. Field of the Invention

The present invention relates to an image pick up unit wherein optical adjustment is performed by means of a motor.

2. Description of the Related Art

A variety of image pick up units have been used wherein optical adjustment is performed by means of a motor.

For example, in an image pick up unit used for a camera head for an endoscope disclosed in Jpn. Pat. Appln. KOKAI Publication No. 2004-97292, a lens frame is inserted into a package frame slidable in the axial direction of an optical axis. The lens frame is moved in the axial direction of an optical axis by interaction between a magnet provided in the package frame and a coil provided in the lens frame, whereby focusing is performed.

In an image pick up unit used in a camera disclosed in Jpn. Pat. Appln. KOKAI Publication No. 2003-131111, a lens frame is inserted into a cylindrical cam, and a cam mechanism is formed between the lens frame and cylindrical cam. The cylindrical cam is rotated about the optical axis by a motor, and the lens frame is moved in the axial direction of the optical axis through the cam mechanism, whereby focusing is performed.

BRIEF SUMMARY OF THE INVENTION

According to an aspect of the invention, an image pick up unit includes: an optical member, a holding member holding the optical member and movable in an axial direction of an optical axis of the optical member; a driving member rotatable about the optical axis; a cam mechanism configured to convert rotation of the driving member about the optical axis to movement of the holding member in the axial direction of the optical axis; a coil provided in the driving member and movable together with the driving member; and a magnetic field generation portion provided along a rotating direction of the coil and configured to generate a magnetic field to interact with a current flowing in the coil to drive the coil in the rotating direction.

According to another aspect of the invention, a medical apparatus includes an image pick up unit including: an optical member, a holding member holding the optical member and movable in an axial direction of an optical axis of the optical member; a driving member rotatable about the optical axis; a cam mechanism configured to convert rotation of the driving member about the optical axis to movement of the holding member in the axial direction of the optical axis; a coil provided in the driving member and movable together with the driving member; and a magnetic field generation portion provided along a rotating direction of the coil and configured to generate a magnetic field to interact with a current flowing in the coil to drive the coil in the rotating direction.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

A first embodiment of the invention will be explained hereinafter with reference to the accompanying drawings FIG. 1-FIG. 2C.

Figure 1:
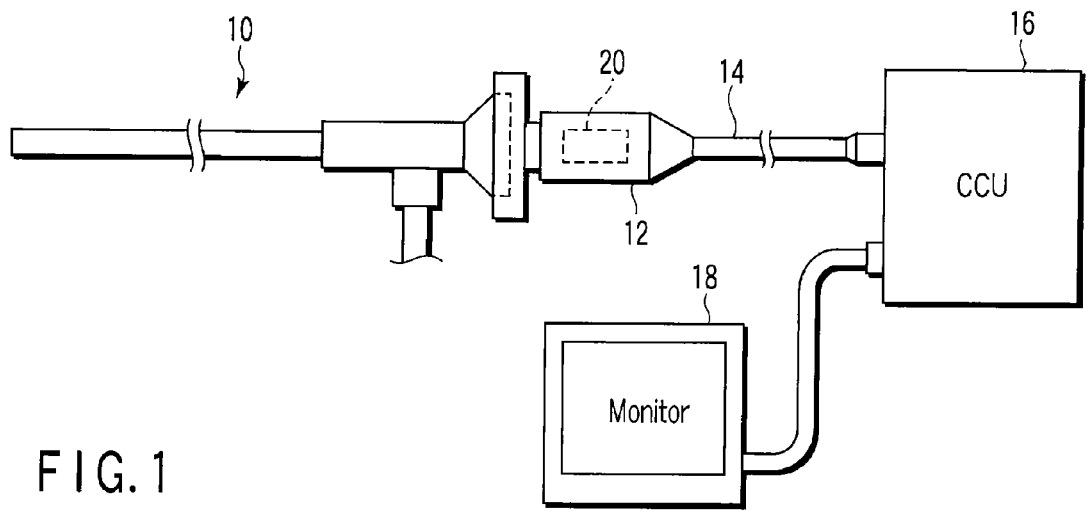
FIG. 1 is a schematic view showing a medical system according to a first embodiment of the invention.

Referring to FIG. 1, a medical system of the embodiment includes an optical endoscope 10. A camera head 12 for picking up an observation image is mounted to an eyepiece of the endoscope 10. The camera head 12 is connected to a camera control unit (CCU) 16 through a camera cable 14. An image signal of the observation image picked up by the camera head 12 is output to the CCU 16. A monitor 18 is connected to the CCU 16. The observation image is displayed in the monitor 18.

An image pick up unit 20 incorporated in the camera head 12 will be explained in detail hereinafter.

Figure 2A:
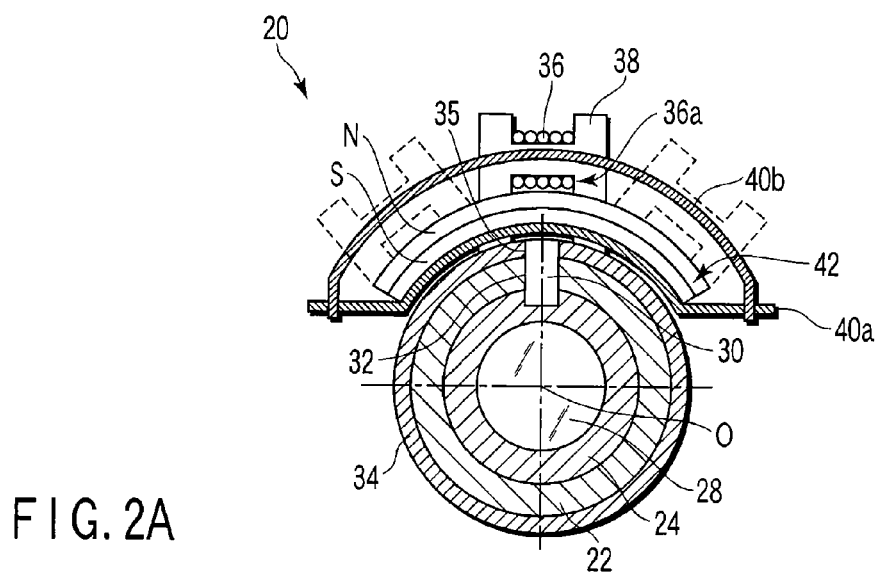
FIG. 2A is a front view showing the image pick up unit partially sectioned transversely according to the first embodiment of the invention.
Figure 2B:
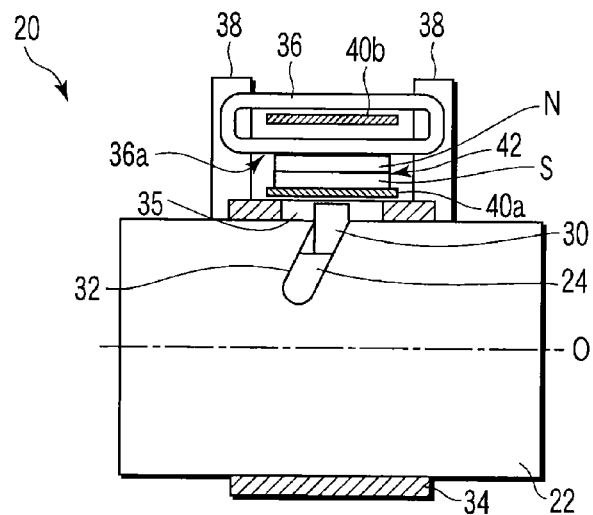
FIG. 2B is a side view showing the image pick up unit partially sectioned longitudinally according to the first embodiment of the invention.
Figure 2C:
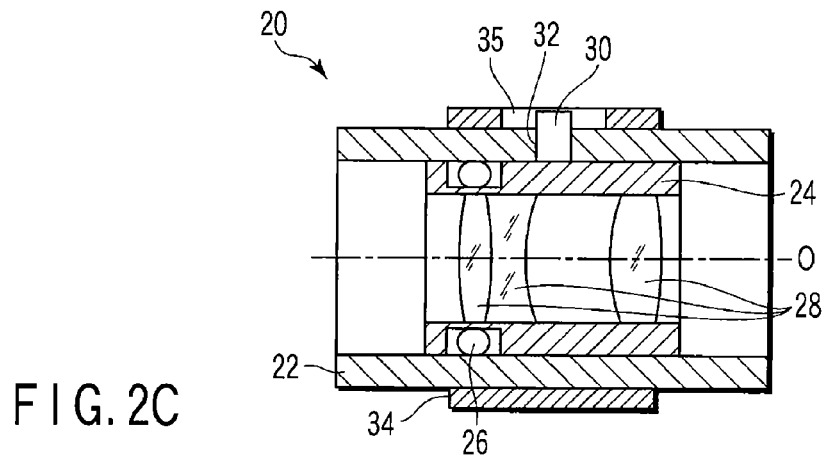
FIG. 2C is a longitudinal sectional view showing the image pick up unit according to the first embodiment of the invention.

Referring to FIGS. 2A-2C, the image pick up unit 20 of the embodiment includes a substantially cylindrical lens barrel 22 fixed to a housing. In the lens barrel 22, a substantially cylindrical lens frame 24 as a holding member is inserted movably in the axial direction and rotatably about the central axis. Inside the lens frame 24, a lens 28 as an optical member is provided. The central axis of the lens frame 24 substantially coincides with the optical axis O of the lens 28. Between the inner circumferential surface of the lens barrel and the outer circumferential surface of the lens frame 24, a regulation member 26 is provided to regulate unnecessary movement of the lens frame 24 with respect to the lens barrel 22. In the embodiment, an O-ring is used as the regulation member 26, but a spring member may be used instead.

A cam pin 30 is projected from the outer circumferential portion of the lens frame 24. The cam pin 30 is inserted into and engaged with a cam groove 32 in the shape of a through groove extending spirally in the lens barrel 22. The projecting end of the cam pin 30 passes through the cam groove 32 and projects from the outer circumferential surface of the lens barrel 22. A substantially cylindrical driving member 34 is provided over the lens barrel 22. In the driving member 34, a driving groove 35 in the shape of a through groove extends in the axial direction. The projecting end of the cam pin 30 is inserted into and engaged with the driving groove 35. The cam pin 30 is movable in the axial direction of the optical axis O in the driving groove 35 and the movement thereof in the peripheral direction about the optical axis O is regulated.

A support member 38 for supporting a coil 36 projects from both ends of the driving member 34. These support members 38 have an "H" shape when viewed in the axial direction of the optical axis O. A wire is wound many times over the horizontal bar portions of one support member 38 and the other support member 38, forming a coil 36. Namely, the transverse cross section of the coil 36 is substantially rectangular.

Outside the driving member 34 and between the support members 38, a bent plate shaped inside yoke 40a extends in the peripheral direction about the optical axis O. On the outer circumferential surface of the inside yoke 40a, a bent plate shaped magnet extending in the peripheral direction about the optical axis O and including a S-pole on the inner circumferential surface side and N-pole on the outer circumferential surface side is superposed, forming a magnetic field generation portion 42. Namely, the magnetic field generation portion 42 is arranged in the shape of an arc about the optical axis O. Outside the magnetic field generation portion 42 and between the support members 38, a bent plate shaped outside yoke 40b extends in the peripheral direction about the optical axis O. The outside yoke 40b passes through the inside of the coil 36 wound around the support members 38, and the coil 36 is rotatable about the optical axis O along the outside yoke 40b. Both ends of the inside yoke 40a and outside yoke 40b are connected.

In the embodiment, a magnetic field characterized by lines of magnetic force extending in the radial direction of the optical axis O from the outer circumferential surface of the magnetic field generation portion 42 to the inner circumferential surface of the outside yoke 40b is contributive to the motor output. In the coil 36, only an inside N-pole side portion 36a arranged between the outer circumferential surface of the magnetic field generation portion 42 and the inner circumferential surface of the outside yoke 40b, in other words, arranged close to the N-pole side of the magnetic field generation portion 42 is contributive to the motor output.

Next, the function of the medical system of the embodiment will be explained.

When an observation image of the endoscope 10 is picked up by means of the camera head 12, focusing is performed by means of the image pick up unit 20. When a current flows in the coil 36, a current flows in the axial direction of the optical axis O in the N-pole side portion 36a of the coil 36 and interacts with a magnetic field characterized by lines of magnetic force extending in the radial direction of the optical axis O from the outer circumferential surface of the magnetic field generation portion 42 to the inner circumferential surface of the outside yoke 40b. As a result, a driving force in the peripheral direction about the optical axis O is generated in the coil 36. By the driving force, the coil 36, support member 38 supporting the coil 36, and driving member 34 connected to the support member 38 are rotated together about the optical axis O. As a result, the cam pin 30 inserted into and engaged with the driving groove 35 of the driving member 34 is driven in the peripheral direction about the optical axis O, and moved along the cam groove 32 of the lens barrel 22, and the lens frame 24 connected to the cam pin 30 is moved in the peripheral direction about the optical axis O and in the axial direction of the optical axis O. The lens 28 is moved in one direction of the axial direction of the optical axis O. When the direction of a current in the coil 36 is reversed, the lens 28 is moved in the reverse direction. The focusing is performed in the way.

After the focusing, the observation image is observed on the monitor 18. At the time, the current to the coil 36 is stopped, but unnecessary movement of the lens frame 24 with respect to the lens barrel 22 is prevented by the regulation member 26 provided between the lens barrel 22 and lens frame 24. Therefore, defocusing during observation is prevented.

The image pick up unit 20 of the medical system of the embodiment provides the following effects.

In the image pick up unit 20, as the cam mechanisms 30 and 32 are formed between the driving member 34 and lens frame 24, unnecessary movement of the lens frame 24 during stop of the motor can be prevented without applying so large slide resistance between the driving member 34 and lens frame 24 so that the lens frame 24 can be moved by a relatively small output of the motor. As the motor and cam mechanisms 30 and 32 are formed as one body, the whole structure is compact and as the motor output directly acts on the cam mechanisms 30 and 32, the motor efficiency is improved. Therefore, focusing can be performed by the relatively small output of the motor, and the image pick up unit 20 can be made compact.

The magnetic field generation portion 42 is arranged in the shape of the arc about the optical axis O, and so compact arrangement is realized about the optical axis O.

Figure 3A:
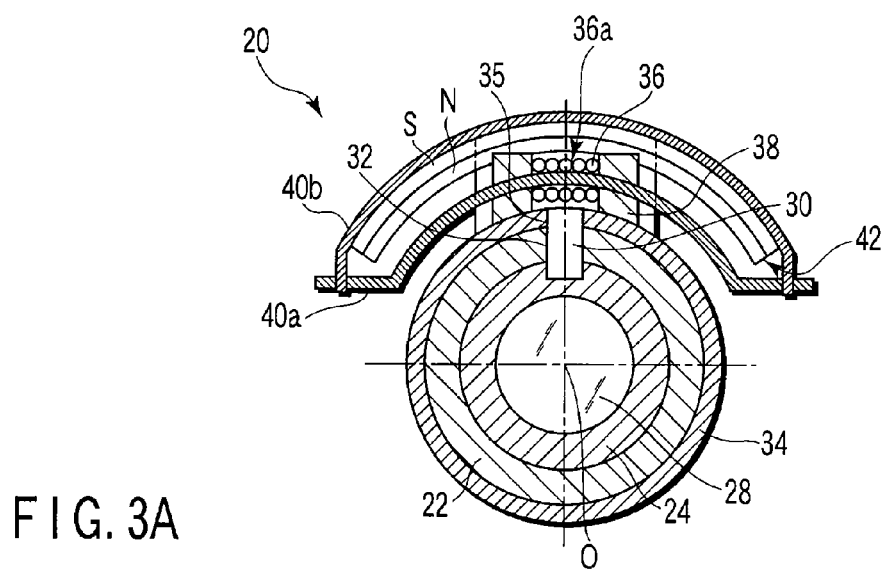
FIG. 3A is a front view showing an image pick up unit partially sectioned transversely according to a second embodiment of the invention.
Figure 3B:
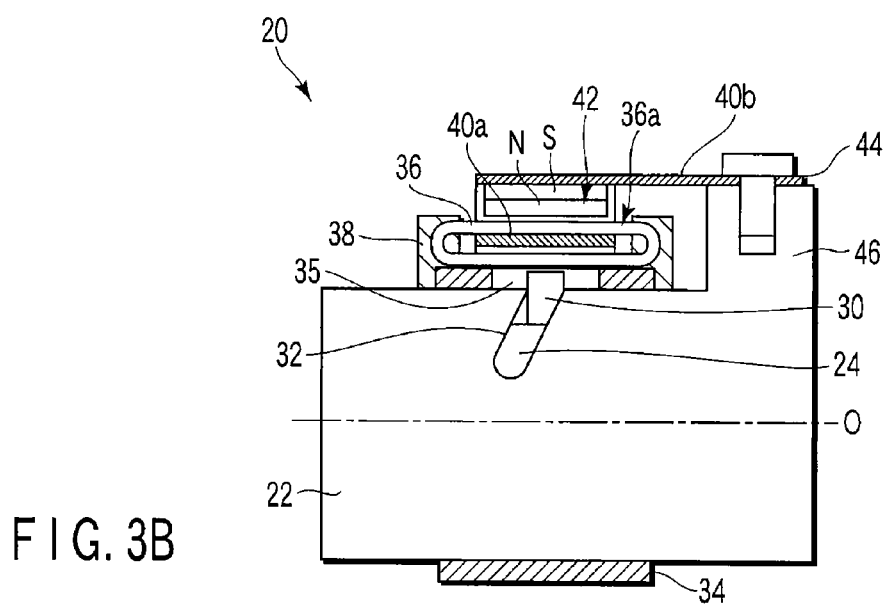
FIG. 3B is a side view showing the image pick up unit partially sectioned longitudinally according to the second embodiment of the invention.
Figure 3C:
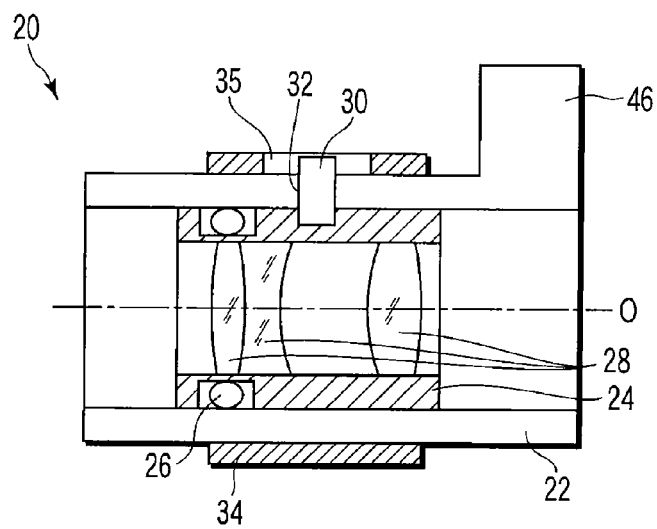
FIG. 3C is a longitudinal sectional view showing the image pick up unit according to the second embodiment of the invention.

FIGS. 3A-3C show a second embodiment of the invention. The same components having the same functions as the first embodiment are given the same reference numerals, and explanation will be omitted.

In the image pick up unit 20 of the embodiment, on the inner circumferential surface of the bent plate shaped outside yoke 40b extending in the peripheral direction about the optical axis O, the bent plate shaped magnet extending in the peripheral direction about the optical axis O and including the S-pole on the outer circumferential surface side and the N-pole on the inner circumferential surface side is superposed, forming the magnetic field generation portion 42. Namely, the magnetic field generation portion 42 is arranged in the shape of the arc about the optical axis O. Inside the magnetic field generation portion 42 and between the support members 38, the bent plate shaped inside yoke 40a extending in the peripheral direction about the optical axis O is arranged. The inside yoke 40a passes through the inside of the coil 36, and the coil 36 is rotatable about the optical axis O along the inside yoke 40a.

The outside yoke 40b is formed with an extension 44 extending in the axial direction of the optical axis O. The outside yoke 40b is fixed to the lens barrel 22 by fixing the extension 44 to a projection 46 provided on the outer circumferential surface of the lens barrel 22 with a screw.

In the embodiment, a magnetic field characterized by lines of magnetic force extending in the radial direction of the optical axis O from the inner circumferential surface of the magnetic field generation portion 42 to the inner circumferential surface of the inside yoke 40a is contributive to the motor output. In the coil 36, only the outside N-pole side portion 36a arranged between the inner circumferential surface of the magnetic field generation portion 42 and the outer circumferential surface of the inside yoke 40a, in other words, arranged close to the N-pole side of the magnetic field generation portion 42 is contributive to the motor output.

The image pick up unit 20 of the medical system of the embodiment provides the following effects.

In the image pick up unit 20 of the embodiment, the magnetic field generation portion 42 is arranged in the shape of the ark about the optical axis O, and the magnetic field intensity is larger in the inside of the magnetic field generation portion 42 than the outside. As the portion interacting with the magnetic field in the coil 36 is arranged on the inside having larger magnetic field intensity, the motor efficiency is improved compared with the case where that portion is arranged on the outside having smaller magnetic field intensity.

Figure 4A:
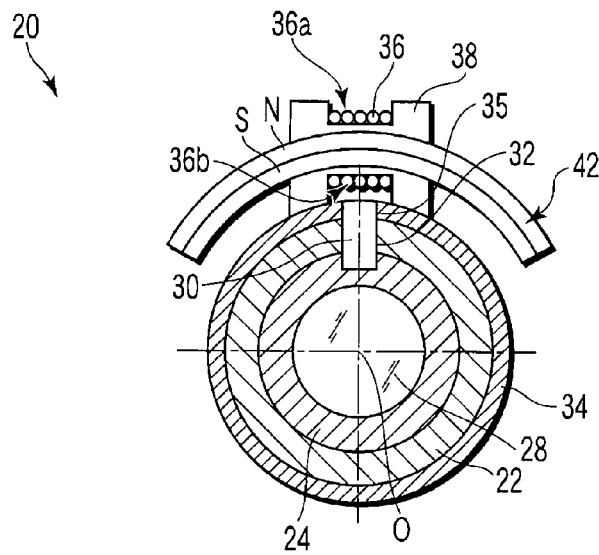
FIG. 4A is a front view showing an image pick up unit partially sectioned transversely according to a third embodiment of the invention.
Figure 4B:
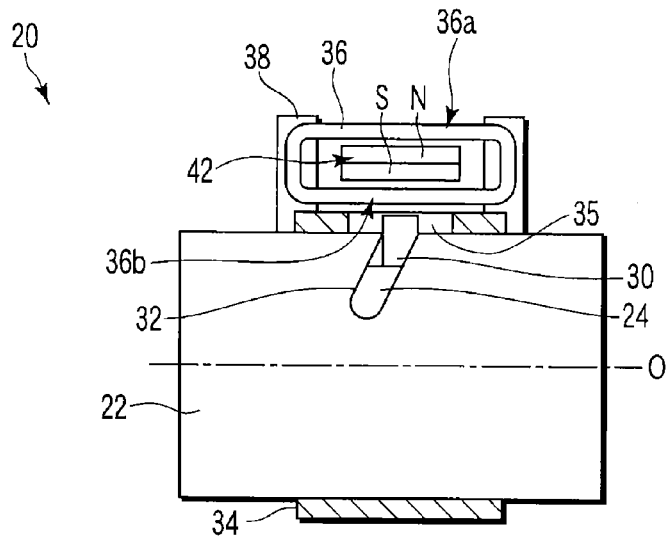
FIG. 4B is a side view showing the image pick up unit partially sectioned longitudinally according to the third embodiment of the invention.
Figure 4C:
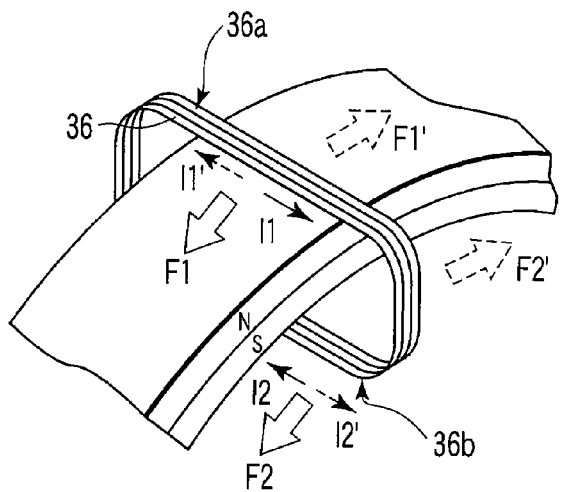
FIG. 4C is a perspective view for explaining a driving force generated in a coil of the image pick up unit of the third embodiment of the invention.

FIGS. 4A-4C show a second embodiment of the invention. The same components having the same functions as the first embodiment are given the same reference numerals, and explanation will be omitted.

The magnetic field generation portion 42 of the embodiment is composed of the bent plate shaped magnet extending in the peripheral direction about the optical axis O outside the driving member 34 and between the support members 38 and including the S-pole on the inner circumferential surface side and N-pole on the outer circumferential surface side. The magnetic field generation portion 42 passes through the inside of the coil 36. The coil 36 is rotatable about the optical axis O along the magnetic field generation portion 42.

In the embodiment, a magnetic field characterized by lines of magnetic force extending from the outer circumferential surface to the inner circumferential surface of the magnetic field generation portion 42 through an external space is contributive to the motor output. In the coil 36, the outside N-pole side portion 36a arranged close to the N-pole side of the magnetic field generation portion 42 and an inside S-pole side portion 36b arranged close to the S-pole side of the magnetic field generation portion 42 are contributive to the motor output.

The function of the image pick up unit 20 of the embodiment will be explained.

Referring to FIG. 4C, when a current flows in the coil 36, a current flows in one axial direction of the optical axis O in the N-pole side portion 36a of the coil 36 as indicated by the arrow I1, and interacts with a magnetic field characterized by lines of magnetic force extending from the outer circumferential surface of a magnetic field generation portion 42, and a driving force is generated in one direction of the peripheral direction about the optical axis O in the N-pole side portion 36a of the coil 36, as indicated by the arrow F1. On the other hand, as indicated by the arrow I2, a current flows in the reverse direction to the axial direction of the optical axis O in the S-pole side portion 36b of the coil 36, and interacts with a magnetic field characterized by lines of magnetic force extending to the inner circumferential surface of the magnetic field generation portion 42, and a driving force is generated in one direction of the peripheral direction about the optical axis O in the S-pole side portion 36b of the coil 36, as indicated by the arrow F2. Both driving forces are in substantially the same direction, and a driving force in the peripheral direction about the optical axis O is generated in the coil 36. When the direction of a current in the coil 36 is reversed, a driving force is generated in the reverse direction (refer to the arrows I1', I2', F1', and F2').

The image pick up unit 20 of the medical system of the embodiment provides the following effects.

In the image pick up unit 20 of the embodiment, a driving force is generated almost in the same direction in both of the N-pole and S-pole side portions 36a and 36b of the coil 36, and the motor efficiency is improved compared with the case where a driving force is generated in one of the pole side portions.

Figure 5A:
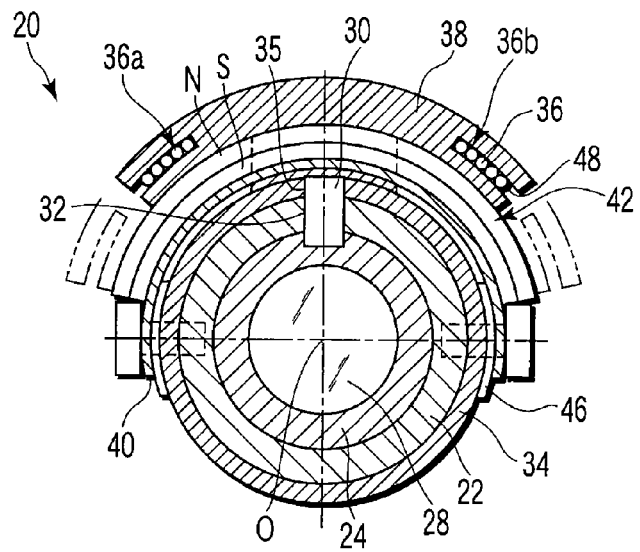
FIG. 5A is a front view showing an image pick up unit partially sectioned transversely according to a fourth embodiment of the invention.
Figure 5B:
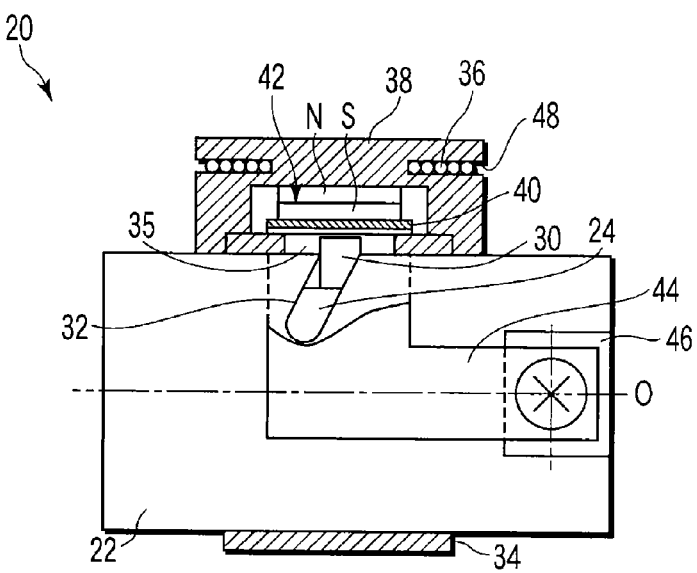
FIG. 5B is a side view showing the image pick up unit partially sectioned longitudinally according to the fourth embodiment of the invention.
Figure 5C:
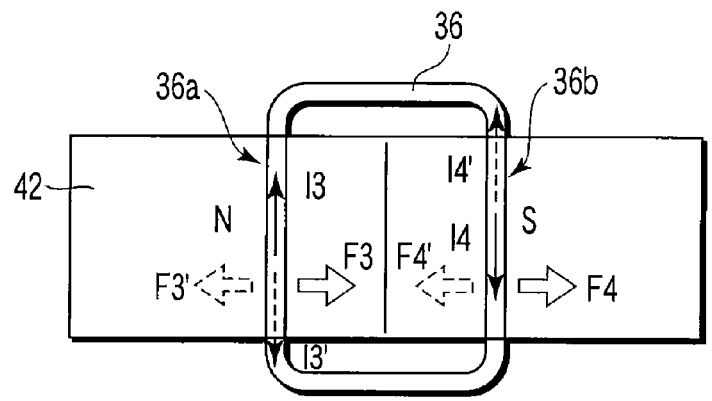
FIG. 5C is a perspective view for explaining a driving force generated in a coil of the image pick up unit of the fourth embodiment of the invention.

FIGS. 5A to 5C show a fourth embodiment of the invention. The same components having the same functions as the first embodiment are given the same reference numerals, and explanation will be omitted.

In the image pick up unit 20 of the embodiment, the support member 38 is formed by connecting a thick bent plate shaped portion having the width extending over a pair of column shaped portions in the axial direction of the optical axis O and extending in the peripheral direction about the optical axis O, to an projecting end of a pair of column shaped portions projecting from both ends of the driving member 34 in the radial direction of the optical axis O. In the bent plate shaped portion of the support member 38, a notch shaped circumferential groove 48 is formed over both side faces and both end faces of the support member 38. In other words, the bent plate shaped portion of the support member 38 is shaped of constriction. The circumferential groove 48 is formed along a circumferential surface about the optical axis O, and the width of the circumferential groove 48 is substantially equal to the outside diameter of the wire of the coil 36. The coil 36 is formed by winding a wire of the coil 36 in the central portion of the constriction to become a rectangle, while the wire is accommodated in the circumferential groove 48. Namely, the wire of the coil 36 is not superposed in the radial direction of the optical axis O, and arranged to include the circumferential surface about the optical axis O.

A bent plate shaped yoke 40 extending in the peripheral direction about the optical axis O is provided outside the driving member 34 and between the column shaped portions of the support member 38. On the outer circumferential surface of the yoke 40, a bent plate shaped first magnet extending in the peripheral direction about the optical axis O and including an S-pole on the inner circumferential surface side and N-pole on the outer circumferential surface side is superposed on one side with respect to the peripheral direction about the optical axis O, and a bent plate shaped second magnet extending in the peripheral direction about the optical axis O and including an N-pole on the inner circumferential surface side and S-pole on the outer circumferential surface side is superposed on the other side with respect to direction about the optical axis O, thereby forming the magnetic field generation portion 42.

At both ends of the yoke 40, an extension 44 extending in the axial direction of the optical axis O is provided. The yoke 40 is fixed to the lens barrel 22 by fixing the extension 44 to the projection 46 provided on the outer circumferential surface of the lens barrel 22 with a screw.

In the embodiment, a magnetic field characterized by lines of magnetic force extending from the N-pole on the outer circumferential surface to the S-pole on the outer circumferential surface of the magnetic field generation portion 42 through an external space is contributive to the motor output. In the coil 36, the N-pole side portion 36a arranged close to the N-pole side of the magnetic field generation portion 42 and extending in the axial direction of the optical axis O, and the S-pole side portion 36b arranged close to the S-pole side of the magnetic field generation portion 42 and extending in the axial direction of the optical axis O are contributive to the motor output.

The function of the image pick up unit 20 of the embodiment will be explained.

Referring to FIG. 5C, when a current flows in the coil 36, a current flows in one axial direction of the optical axis O in the N-pole side portion 36a of the coil 36 as indicated by the arrow I3, and interacts with a magnetic field characterized by lines of magnetic force extending from the N-pole on the outer circumferential surface of the magnetic field generation portion 42, and a driving force is generated in one direction of the peripheral direction about the optical axis O in the N-pole side portion 36a of the coil 36, as indicated by the arrow F3. On the other hand, as indicated by the arrow I4, the current flows in the reverse direction to the axial direction of the optical axis O in the S-pole side portion 36b of the coil 36, and interacts with a magnetic field characterized by lines of magnetic force extending to the S-pole of the magnetic field generation portion 42, and a driving force is generated in one direction of the peripheral direction about the optical axis O in the S-pole side portion 36b of the coil 36, as indicated by the arrow F4. Both driving forces are in substantially the same direction, and a driving force is generated in the coil 36 in the peripheral direction about the optical axis O. When the direction of a current in the coil 36 is reversed, a driving force is generated in the reverse direction (refer to the arrows I3', I4', F3', and F4').

The image pick up unit 20 of the medical system of the embodiment provides the following effects.

In the image pick up unit 20 of the embodiment, as in the image pick up unit 20 of the third embodiment, the driving force is generated almost in the same direction in both of the N-pole and S-pole side portions 36a and 36b of the coil 36, and the motor efficiency is improved.

As the coil 36 is arranged so that the wire of the coil 36 includes the circumferential surface about the optical axis O and the wire is not superposed in the radial direction of the optical axis O, the image pick up unit 20 can be made to have a small diameter.

Figure 6A:
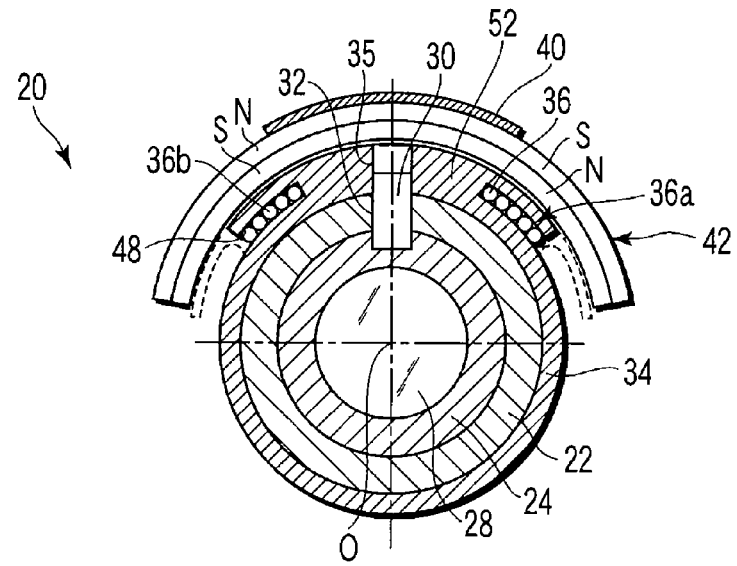
FIG. 6A is a front view showing an image pick up unit partially sectioned transversely according to a fifth embodiment of the invention.
Figure 6B:
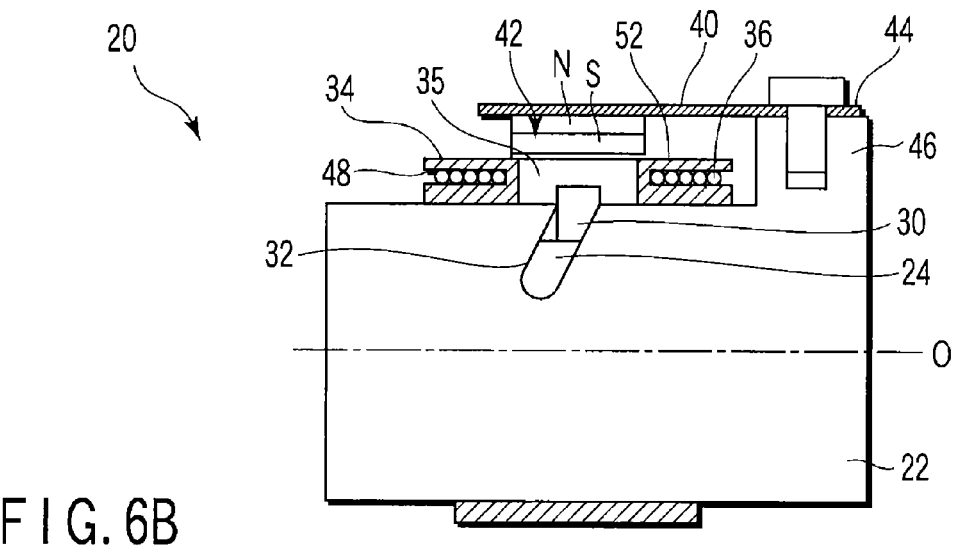
FIG. 6B is a side view showing the image pick up unit partially sectioned longitudinally according to the fifth embodiment of the invention.

FIGS. 6A and 6B show a fifth embodiment of the invention. The same components having the same functions as the first embodiment are given the same reference numerals, and explanation will be omitted.

On the outer circumferential surface of the driving member 34 of the embodiment, a thick support portion 52 having a similar shape as the bent plate shaped portion of the support member 38 in the fourth embodiment is formed, and the coil 36 is wound around the support portion 52 in a similar form as in the fourth embodiment. The yoke 40 arranged outside the support portion 52 and extending in the axial direction of the optical axis O is fixed to the projection 46 provided on the outer circumferential surface of the lens barrel 22 with a screw. The magnetic field generation portion 42 is provided on the inner circumferential surface of the yoke 40. In the magnetic field generation portion 42, the bent plate shaped first magnet extending in the peripheral direction about the optical axis O and including the S-pole on the inner circumferential surface side and N-pole on the outer circumferential surface side is arranged on one side with respect to the peripheral direction about the optical axis O, and the bent plate shaped second magnet extending in the peripheral direction about the optical axis O and including the N-pole on the inner circumferential surface side and S-pole on the outer circumferential surface side is arranged on the other side with respect to the peripheral direction about the optical axis O. Namely, the magnetic field generation portion 42 is arranged in the shape of the arc about the optical axis O.

In the embodiment, a magnetic field characterized by lines of magnetic force extending from the N-pole on the inner circumferential surface to the S-pole on the inner circumferential surface of the magnetic field generation portion 42 through an external space is contributive to the motor output. In the coil 36, as in the fourth embodiment, the N-pole side portion 36a arranged close to the N-pole side of the magnetic field generation portion 42 and extending in the axial direction of the optical axis O, and the S-pole side portion 36b which is arranged close to the S-pole side of the magnetic field generation portion 42 and extending in the axial direction of the optical axis O are contributive to the motor output.

The image pick up unit 20 of the medical system of the embodiment provides the following effects.

In the image pick up unit 20 of the embodiment, as in the second embodiment, as the magnetic field intensity is larger inside of the magnetic field generation portion 42 and the coil 36 is arranged inside where the magnetic field intensity is large, the motor efficiency is improved.

Further, as in the fourth embodiment, a driving force is generated in substantially the same direction in both of N-pole and S-pole side portions 36a and 36b of the coil 36, and the motor efficiency is improved.

As the driving member 34 functions also as a support member to support the coil and so a support member is unnecessary, the number of parts is decreased.

Focusing is performed in the image pick up unit of the above-mentioned embodiment. Various optical adjustments such as variable power adjustment may be performed in the image pick up unit of the invention.

The image pick up unit of the invention is applicable to any image pick up apparatus. The image pick up unit of the invention uses a cam mechanism to drive a lens frame, and precise and stable optical adjustment is possible though reactivity is low, compared with the case of driving a lens frame in the axial direction of an optical axis by providing a coil or a magnet directly in the lens frame. Therefore, the image pick up unit of the invention is particularly suitable for an image pick up apparatus not requiring frequent optical adjustment, for example, an endoscope and the above mentioned camera head for an endoscope. When the image pick up unit of the invention is used in the endoscope, the unit is incorporated at a distal end of the endoscope.

Autoclave sterilization using high-temperature and high-pressure vapor may be applied to an endoscope and a camera head for an endoscope after use. Important parts such as an image pick up device used in the endoscope or the camera head for the endoscope are provided in an airtight package not to be directly exposed to such high-temperature and high-pressure vapor, but temporarily heated to a high temperature during autoclave sterilization. In a DC motor and a stepping motor used for a general use camera and the like, the motor itself includes a rotational portion, and grease is used to make the rotation smooth. When such motors is placed under high-temperature environment like that during autoclave sterilization, grease is dispersed to exert a bad influence on a rotational function, and therefore they are difficult to use in the endoscope or the camera head for the endoscope requiring adaptation to autoclave sterilization. Contrarily, the coil and magnet used in the present invention has sufficient heat-resistance to a high temperature during autoclave sterilization, and are therefore adaptable to autoclave sterilization. Therefore, the image pick up unit of the present invention is optimum for the endoscope and the camera head for the endoscope.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image pick up unit comprising:
   an optical member;
   a holding member holding the optical member and movable in an axial direction of an optical axis of the optical member;
   a driving member rotatable about the optical axis in a peripheral direction of the optical axis;
   a cam mechanism configured to convert rotation of the driving member about the optical axis in the peripheral direction to movement of the holding member in the axial direction;
   a coil provided in the driving member, movable together with the driving member and including one pole side portion in which wire parts of the coil extend in the axial direction and are arranged side by side in the peripheral direction; and
   a magnetic field generation portion extending in the peripheral direction and including one pole portion configured to generate a magnetic field to interact with a current flowing in the one pole side portion to drive the coil in the peripheral direction.

2. The image pick up unit according to claim 1,
   wherein the one pole portion is arranged outside in a radial direction of the optical axis in the magnetic field generation portion,
   the image pick up unit further comprising a yoke extending in the peripheral direction and arranged outside in the radial direction relative to the one pole portion,
   the one pole side portion is arranged between the one pole portion and the yoke in the radial direction, and
   a magnetic field characterized by lines of magnetic force extending in the radial direction between the one pole portion and the yoke is to interact with a current flowing in the axial direction in the one pole side portion to generate a driving force in the peripheral direction.

3. The image pick up unit according to claim 1,
   wherein the one pole portion is arranged inside in a radial direction of the optical axis in the magnetic field generation portion,
   the image pick up unit further comprising a yoke extending in the peripheral direction and arranged inside in the radial direction relative to the one pole portion,
   the one pole side portion is arranged between the one pole portion and the yoke in the radial direction, and
   a magnetic field characterized by lines of magnetic force extending in the radial direction between the one pole portion and the yoke is to interact with a current flowing in the axial direction in the one pole side portion to generate a driving force in the peripheral direction.

4. The image pick up unit according to claim 1,
   wherein the coil further includes the other pole side portion in which wire parts of the coil extends in the axial direction and are arranged side by side in the peripheral direction,
   the magnetic field generation portion further includes the other pole portion wherein the one pole portion is arranged outside in a radial direction of the optical axis in the magnetic field generation portion and the other pole portion is arranged inside in the radial direction in the magnetic field generation portion,
   the one pole side portion is arranged outside in the radial direction relative to the one pole portion and the other pole side portion is arranged inside in the radial direction relative to the other pole portion, and
   a magnetic field characterized by lines of magnetic force extending in one radial direction with respect to the one pole portion is to interact with a current flowing in one axial direction in the one pole side portion to generate a driving force in one peripheral direction and a magnetic field characterized by lines of magnetic force extending in the other radial direction opposite to the one radial direction with respect to the other pole portion is to interact with a current flowing in the other axial direction opposite to the one axial direction in the other pole side portion to generate a driving force in the one peripheral direction.

5. The image pick up unit according to claim 1,
   wherein the coil further includes the other pole side portion in which wire parts of the coil extends in the axial direction and are arranged side by side in the peripheral direction,
   the magnetic field generation portion further includes the other pole portion wherein the one pole portion is arranged on one side in the peripheral direction in the magnetic field generation portion and the other pole portion is arranged on the other side opposite to the one side in the peripheral direction in the magnetic field generation portion,
   the one pole side portion is arranged outside in the radial direction relative to the one pole portion and the other pole side portion is arranged outside in the radial direction relative to the other pole portion, and
   a magnetic field characterized by lines of magnetic force extending in one radial direction with respect to the one pole portion is to interact with a current flowing in one axial direction in the one pole side portion to generate a driving force in one peripheral direction and a magnetic field characterized by lines of magnetic force extending in the other radial direction opposite to the one radial direction with respect to the other pole portion is to interact with a current flowing in the other axial direction opposite to the one axial direction in the other pole side portion to generate a driving force in the one peripheral direction.

6. The image pick up unit according to claim 1,
   wherein the coil further includes the other pole side portion in which wire parts of the coil extends in the axial direction and are arranged side by side in the peripheral direction,
   the magnetic field generation portion further includes the other pole portion wherein the one pole portion is arranged on one side in the peripheral direction in the magnetic field generation portion and the other pole portion is arranged on the other side opposite to the one side in the peripheral direction in the magnetic field generation portion,
   the one pole side portion is arranged inside in the radial direction relative to the one pole portion and the other pole side portion is arranged inside in the radial direction relative to the other pole portion, and a magnetic field characterized by lines of magnetic force extending in one radial direction with respect to the one pole portion is to interact with a current flowing in one axial direction in the one pole side portion to generate a driving force in one peripheral direction and a magnetic field characterized by lines of magnetic force extending in the other radial direction opposite to the one radial direction with respect to the other pole portion is to interact with a current flowing in the other axial direction opposite to the one axial direction in the other pole side portion to generate a driving force in the one peripheral direction.

7. A medical apparatus comprising an image pick up unit including:

an optical member;

a holding member holding the optical member and movable in an axial direction of an optical axis of the optical member;

a driving member rotatable about the optical axis in a peripheral direction of the optical axis;

a cam mechanism configured to convert rotation of the driving member about the optical axis in the peripheral direction to movement of the holding member in the axial direction;

a coil provided in the driving member, movable together with the driving member and including one pole side portion in which wire parts of the coil extends in the axial direction and are arranged side by side in the peripheral direction; and a magnetic field generation portion extending in the peripheral direction and including one pole portion configured to generate a magnetic field to interact with a current flowing in the one pole side portion to drive the coil in the peripheral direction.

* * * * *